(12) United States Patent
Gross et al.

(10) Patent No.: US 8,065,021 B2
(45) Date of Patent: *Nov. 22, 2011

(54) ELECTRODE ASSEMBLY FOR NERVE CONTROL

(75) Inventors: Yossi Gross, Moshav Mazor (IL); Shai Ayal, Jerusalem (IL); Ehud Cohen, Ganei Tivka (IL)

(73) Assignee: Bio Control Medical (B.C.M.) Ltd., Yahud (IL)

( * ) Notice: Subject to any disclaimer, the term of this patent is extended or adjusted under 35 U.S.C. 154(b) by 428 days.

This patent is subject to a terminal disclaimer.

(21) Appl. No.: 11/981,301

(22) Filed: Oct. 30, 2007

(65) Prior Publication Data

US 2008/0161895 A1    Jul. 3, 2008

Related U.S. Application Data

(63) Continuation of application No. 10/948,516, filed on Sep. 23, 2004, now Pat. No. 7,346,398, which is a continuation of application No. 10/205,474, filed on Jul. 24, 2002, now Pat. No. 6,907,295.

(60) Provisional application No. 60/383,157, filed on May 23, 2002.

(51) Int. Cl.
   *A61N 1/04* (2006.01)
(52) U.S. Cl. ..................... 607/118; 607/117
(58) Field of Classification Search .......... 607/117–118
   See application file for complete search history.

(56) References Cited

U.S. PATENT DOCUMENTS

| | | | |
|---|---|---|---|
| 4,026,300 A | 5/1977 | DeLuca et al. | |
| 4,602,624 A | 7/1986 | Naples et al. | |
| 4,628,942 A * | 12/1986 | Sweeney et al. | 607/118 |
| 5,215,089 A * | 6/1993 | Baker, Jr. | 600/377 |
| 5,400,784 A | 3/1995 | Durand et al. | |
| 5,423,872 A | 6/1995 | Cigaina et al. | |
| 5,487,756 A | 1/1996 | Kallesoe et al. | |
| 5,505,201 A | 4/1996 | Grill et al. | |
| 5,634,462 A | 6/1997 | Tyler et al. | |
| 5,824,027 A | 10/1998 | Hoffer et al. | |

(Continued)

FOREIGN PATENT DOCUMENTS

DE    198 47 446    4/2000

(Continued)

OTHER PUBLICATIONS

Manfredi, M., (1970) "Differential block of conduction of larger fibers in peripheral nerve by direct current," *Arch. Ital. Biol.* 108:52-71.

(Continued)

*Primary Examiner* — Niketa Patel
*Assistant Examiner* — Joseph Stoklosa
(74) *Attorney, Agent, or Firm* — Sughrue Mion, PLLC

(57) ABSTRACT

Apparatus is provided for applying current to a nerve. A cathode is adapted to be placed in a vicinity of a cathodic longitudinal site of the nerve and to apply a cathodic current to the nerve. A primary inhibiting anode is adapted to be placed in a vicinity of a primary anodal longitudinal site of the nerve and to apply a primary anodal current to the nerve. A secondary inhibiting anode is adapted to be placed in a vicinity of a secondary anodal longitudinal site of the nerve and to apply a secondary anodal current to the nerve, the secondary anodal longitudinal site being closer to the primary anodal longitudinal site than to the cathodic longitudinal site.

16 Claims, 6 Drawing Sheets

U.S. PATENT DOCUMENTS

| | | | |
|---|---|---|---|
| 5,833,664 | A | 11/1998 | Seare, Jr. |
| 5,938,596 | A | 8/1999 | Woloszko et al. |
| 6,600,956 | B2 | 7/2003 | Maschino et al. |
| 6,907,295 | B2 | 6/2005 | Gross et al. |
| 7,076,307 | B2 | 7/2006 | Boveja et al. |
| 7,218,971 | B2 | 5/2007 | Heil et al. |
| 7,346,398 | B2 | 3/2008 | Gross et al. |
| 7,778,703 | B2 | 8/2010 | Gross et al. |
| 2003/0045909 | A1 | 3/2003 | Gross et al. |
| 2003/0050677 | A1 | 3/2003 | Gross et al. |
| 2006/0136024 | A1 | 6/2006 | Cohen et al. |
| 2008/0132983 | A1 | 6/2008 | Cohen et al. |

FOREIGN PATENT DOCUMENTS

| | | |
|---|---|---|
| EP | 0 688 577 | 12/1995 |
| EP | 0 865 800 | 9/1998 |
| EP | 1 785 160 | 5/2007 |
| WO | WO 01/10357 | 2/2001 |
| WO | WO 03/099373 | 12/2003 |
| WO | WO 04/110550 | 12/2004 |
| WO | WO 2008/007360 | 1/2008 |

OTHER PUBLICATIONS

Zi-Ping, F. and Mortimer, T., (1991) "Selective Activation of Small Motor Axons by Quasitrapezodial Current Pulses," *IEEE Transactions on Biomedical Engineering* 38(2):168-171.

Office Action dated Jun. 27, 2008 which was issued during the prosecution of Applicant's U.S. Appl. No. 10/205,475.

Office Action, issued Oct. 24, 2008, in connection with U.S. Appl. No. 11/022,011, filed Dec. 22, 2004.

Supplemental European Search Report, issued Nov. 4, 2009, in connection with European Patent Application No. 03723040.6, filed May 23, 2003, BioControl Medical Ltd.

European Search Report, issued Aug. 27, 2009, in connection with European Patent Application No. 09251749.9, filed Jul. 7, 2009, BioControl Medical, Ltd.

Office Action, issued Dec. 8, 2009, in connection with U.S. Appl. No. 11/347,120, filed Feb. 2, 2006.

Sweeney, J.D., et al., "An asymmetric two electrode cuff for generation of unidirectionally propagated action potentials," *IEEE Transactions on Biomedical Engineering*, vol. BME-33(6) (1986).

An Office Action dated Nov. 1, 2007, which issued during the prosecution of Applicant's U.S. Appl. No. 10/205,475.

Jones, et al., "Heart rate responses to selective stimulation of cardiac vagal C fibres in anaesthetized cats, rats and rabbits", Journal of Physiology (1995), 489.1 pp. 203-214.

Jones, et al., "Activity of C fibre cardiac vagal efferents in anaesthetized cats and rats", Journal of Physiology (1998), 507.3, pp. 869-880.

Office Action issued Apr. 15, 2009 during the prosecution of U.S. Appl. No. 11/347,120.

An Office Action dated Jan. 21, 2011, which issued during the prosecution of Applicant's U.S. Appl. No. 12/589,132.

Goodall EV et al., "Position-selective activation of peripheral nerve fibers with a cuff electrode," IEEE Trans Biomed Eng, 43(8):851-6 (1996).

An Official Action dated May 23, 2011, which issued during the prosecution of Applicant's U.S. Appl. No. 11/978,776.

An Extended European Search Report dated Jun. 6, 2011, which issued during the prosecution of Applicant's European Patent Application No. 11002403.

An Official Action dated Jun. 7, 2011, which issued during the prosecution of Applicant's U.S. Appl. No. 12/589,132.

\* cited by examiner

ELECTRODE ASSEMBLY FOR NERVE CONTROL

CROSS-REFERENCES TO RELATED APPLICATIONS

The present patent application is a continuation of U.S. Ser. No. 10/948,516, filed Sep. 23, 2004 (now U.S. Pat. No. 7,346, 398), which is a continuation of U.S. Ser. No. 10/205,474, filed Jul. 24, 2002 (now U.S. Pat. No. 6,907,295), which (a) claims the benefit of U.S. Provisional Application No. 60/383,157, filed May 23, 2002, which is assigned to the assignee of the present patent application and is incorporated herein by reference, and (b) is related to U.S. Ser. No. 10/205,475, filed Jul. 24, 2002, which is assigned to the assignee of the present patent application and is incorporated herein by reference.

FIELD OF THE INVENTION

The present invention relates generally to electrical stimulation of tissue, and specifically to methods and devices for regulating the stimulation of nerves.

BACKGROUND OF THE INVENTION

As defined by Rattay, in the article, "Analysis of models for extracellular fiber stimulation," IEEE Transactions on Biomedical Engineering, Vol. 36, no. 2, p. 676, 1989, which is incorporated herein by reference, the activation function (AF) is the second spatial derivative of the electric potential along an axon. In the region where the activation function is positive, the axon depolarizes, and in the region where the activation function is negative, the axon hyperpolarizes. If the activation function is sufficiently positive, then the depolarization will cause the axon to generate an action potential; similarly, if the activation function is sufficiently negative, then local blocking of action potentials transmission occurs. The activation function depends on the current applied, as well as the geometry of the electrodes and of the axon.

For a given electrode geometry, the equation governing the electrical potential is:

$\nabla(\sigma \nabla U) = 4\pi j$, where U is the potential, σ is the conductance tensor specifying the conductance of the various materials (electrode housing, axon, intracellular fluid, etc.), and j is a scalar function representing the current source density specifying the locations of current injection. The activation function is found by solving this partial differential equation for U. If the axon is defined to lie in the z direction, then the activation function is:

$$AF = \frac{\partial^2 U}{\partial z^2}.$$

In a simple, illustrative example of a point electrode located a distance d from the axis of an axon in a uniformly-conducting medium with conductance σ, the two equations above are solvable analytically, to yield:

$$AF = \frac{I_{el}}{4\pi\sigma} \cdot \frac{2z^2 - d^2}{(z^2 + d^2)^{2.5}},$$

where $I_{el}$ is the electrode current. It is seen that when σ and d are held constant, and for a constant positive $I_{el}$ (to correspond to anodal current), the minimum value of the activation function is negative, and is attained at z=0, i.e., at the point on the nerve closest to the source of the anodal current. Thus, the most negative point on the activation function corresponds to the place on a nerve where hyperpolarization is maximized, namely at the point on the nerve closest to the anode.

Additionally, this equation predicts positive "lobes" for the activation function on either side of z=0, these positive lobes peaking in their values at a distance which is dependent on each of the other parameters in the equation. The positive values of the activation function correspond to areas of depolarization, a phenomenon typically associated with cathodic current, not anodal current. However, it has been shown that excess anodal current does indeed cause the generation of action potentials adjacent to the point on a nerve corresponding to z=0, and this phenomenon is therefore called the "virtual cathode effect." (An analogous, but reverse phenomenon, the "virtual anode effect" exists responsive to excess cathodic stimulation.)

U.S. Pat. No. 6,230,061 to Hartung, which is incorporated herein by reference, describes an electrode arrangement for stimulating the heart by means of: (a) an implantable cardiac pacemaker, (b) a first electrode, coupled to a first output of the pacemaker via an intracardiac electrode line, and (c) a second electrode, for transmitting electrical stimulation pulses to the heart tissue, coupled to a second output of the pacemaker via the electrode line. The voltage pulses at the two electrodes have differing polarities relative to a third electrode. The first and second electrodes are arranged on the electrode line in such a way that the electrical dipole field which forms is distorted towards the stimulation point in such a way that a raised gradient above the stimulus threshold is formed there.

A number of patents and articles describe methods and devices for stimulating nerves to achieve a desired effect. Often these techniques include a design for an electrode or electrode cuff.

U.S. Pat. No. 4,608,985 to Crish et al. and U.S. Pat. No. 4,649,936 to Ungar et al., which are incorporated herein by reference, describe electrode cuffs for selectively blocking orthodromic action potentials passing along a nerve trunk, in a manner intended to avoid causing nerve damage.

PCT Patent Publication WO 01/10375 to Felsen et al., which is incorporated herein by reference, describes apparatus for modifying the electrical behavior of nervous tissue. Electrical energy is applied with an electrode to a nerve in order to selectively inhibit propagation of an action potential.

U.S. Pat. No. 5,755,750 to Petruska et al., which is incorporated herein by reference, describes techniques for selectively blocking different size fibers of a nerve by applying direct electric current between an anode and a cathode that is larger than the anode.

The following articles, which are incorporated herein by reference, may be of interest:

Ungar I J et al., "Generation of unidirectionally propagating action potentials using a monopolar electrode cuff," Annals of Biomedical Engineering, 14:437-450 (1986)

Sweeney J D et al., "An asymmetric two electrode cuff for generation of unidirectionally propagated action potentials," IEEE Transactions on Biomedical Engineering, vol. BME-33(6) (1986)

Sweeney J D et al., "A nerve cuff technique for selective excitation of peripheral nerve trunk regions," IEEE Transactions on Biomedical Engineering, 37(7) (1990)

Naples G G et al., "A spiral nerve cuff electrode for peripheral nerve stimulation," by IEEE Transactions on Biomedical Engineering, 35(11) (1988)

van den Honert C et al., "Generation of unidirectionally propagated action potentials in a peripheral nerve by brief stimuli," Science, 206:1311-1312 (1979)

van den Honert C et al., "A technique for collision block of peripheral nerve: Single stimulus analysis," MP-11, IEEE Trans. Biomed. Eng. 28:373-378 (1981)

van den Honert C et al., "A technique for collision block of peripheral nerve: Frequency dependence," MP-12, IEEE Trans. Biomed. Eng. 28:379-382 (1981)

Rijkhoff N J et al., "Acute animal studies on the use of anodal block to reduce urethral resistance in sacral root stimulation," IEEE Transactions on Rehabilitation Engineering, 2(2):92 (1994)

Mushahwar V K et al., "Muscle recruitment through electrical stimulation of the lumbo-sacral spinal cord," IEEE Trans Rehabil Eng, 8(1):22-9 (2000)

Deurloo K E et al., "Transverse tripolar stimulation of peripheral nerve: a modelling study of spatial selectivity," Med Biol Eng Comput, 36(1):66-74 (1998)

Tarver W B et al., "Clinical experience with a helical bipolar stimulating lead," Pace, Vol. 15, October, Part II (1992)

In physiological muscle contraction, nerve fibers are recruited in the order of increasing size, from smaller-diameter fibers to progressively larger-diameter fibers. In contrast, artificial electrical stimulation of nerves using standard techniques recruits fibers in a larger- to smaller-diameter order, because larger-diameter fibers have a lower excitation threshold. This unnatural recruitment order causes muscle fatigue and poor force gradation. Techniques have been explored to mimic the natural order of recruitment when performing artificial stimulation of nerves to stimulate muscles.

Fitzpatrick et al., in "A nerve cuff design for the selective activation and blocking of myelinated nerve fibers," Ann. Conf. of the IEEE Eng. in Medicine and Biology Soc, 13(2), 906 (1991), which is incorporated herein by reference, describe a tripolar electrode used for muscle control. The electrode includes a central cathode flanked on its opposite sides by two anodes. The central cathode generates action potentials in the motor nerve fiber by cathodic stimulation. One of the anodes produces a complete anodal block in one direction so that the action potential produced by the cathode is unidirectional. The other anode produces a selective anodal block to permit passage of the action potential in the opposite direction through selected motor nerve fibers to produce the desired muscle stimulation or suppression.

The following articles, which are incorporated herein by reference, may be of interest:

Rijkhoff N J et al., "Orderly recruitment of motoneurons in an acute rabbit model," Ann. Conf. of the IEEE Eng., Medicine and Biology Soc., 20(5):2564 (1998)

Rijkhoff N J et al., "Selective stimulation of small diameter nerve fibers in a mixed bundle," Proceedings of the Annual Project Meeting Sensations/Neuros and Mid-Term Review Meeting on the TMR-Network Neuros, Apr. 21-23, 1999, pp. 20-21 (1999)

Baratta R et al., "Orderly stimulation of skeletal muscle motor units with tripolar nerve cuff electrode," IEEE Transactions on Biomedical Engineering, 36(8):836-43 (1989)

The following articles, which are incorporated herein by reference, describe techniques using point electrodes to selectively excite peripheral nerve fibers distant from an electrode without exciting nerve fibers close to the electrode:

Grill W M et al., "Inversion of the current-distance relationship by transient depolarization," IEEE Trans Biomed Eng, 44(1):1-9 (1997)

Goodall E V et al., "Position-selective activation of peripheral nerve fibers with a cuff electrode," IEEE Trans Biomed Eng, 43(8):851-6 (1996)

Veraart C et al., "Selective control of muscle activation with a multipolar nerve cuff electrode," IEEE Trans Biomed Eng, 40(7):640-53 (1993)

SUMMARY OF THE INVENTION

It is an object of some aspects of the present invention to provide improved apparatus and methods for stimulating a nerve.

It is a further object of some aspects of the present invention to provide improved methods and apparatus for configuring an electrode assembly.

It is still a further object of some aspects of the present invention to provide improved methods and apparatus for driving an electrode assembly to apply current to a nerve.

In preferred embodiments of the present invention, an electrode assembly for applying current to a nerve comprises a cathode, a primary inhibiting anode and a secondary inhibiting anode, which are fixed within a housing. The cathode, near one end of the housing, is placed on or near the nerve, over a "cathodic longitudinal site" of the nerve, and is driven by a control unit to apply a cathodic current to the nerve. The primary inhibiting anode, adjacent to the cathode in the housing, is placed on or over a "primary anodal longitudinal site" of the nerve, and is driven to apply a primary anodal current to the nerve. The secondary inhibiting anode, which is separated from the cathode by the primary inhibiting anode, is placed on or over a "secondary anodal longitudinal site" of the nerve, and applies a secondary anodal current to the nerve.

Typically, the cathodic current applied at the cathodic longitudinal site stimulates fibers within the nerve to generate action potentials which travel in both directions within the nerve—i.e., towards the anodes ("the anodal direction"), and in the opposite direction, out of the housing, towards a target ("the target direction"). The anodal current, by contrast, is typically applied so as to inhibit the action potentials which were generated at the cathodic longitudinal site and which subsequently traveled in the anodal direction.

For most applications, the secondary anodal current is of lower magnitude than the primary anodal current. In this manner, the "virtual cathode" effect induced by the primary anodal current is minimized. As described in the Background section of the present patent application, the virtual cathode effect can stimulate—rather than block—the generation of action potentials in fibers in a region adjacent to the application of anodal current of a sufficiently high magnitude. In accordance with a preferred embodiment of the present invention, application of the primary and secondary anodal currents in appropriate ratios is configured to generally minimize the virtual cathode effect. Typically, but not necessarily, the ratio of the primary to the secondary anodal current ranges from 5:1 to 10:1.

In a preferred embodiment, a tertiary inhibiting anode is employed to reduce any virtual cathode effect which may be induced by the secondary inhibiting anode. For example, relative to a normalized cathodic current of −1, the primary inhibiting anode, secondary inhibiting anode, and tertiary inhibiting anode may be configured to apply respective currents of 0.66, 0.25, and 0.09. For some applications, the various anodes are independently driven by a control unit, so as to optimize the minimization of the virtual cathode effect and the maximization (when appropriate) of the anodally-induced hyperpolarization. Alternatively, fixed ratios are predefined for the currents applied by the anodes, and are set in hardware, e.g., by a set of resistors which link a single lead coming from the control unit to the respective anodes.

In a preferred embodiment, an elongated anode replaces the anodes described hereinabove. The elongated anode, when placed on or over a nerve, preferably has at least two levels of electrical impedance associated therewith, between respective sites on the elongated anode and the nerve. Most preferably, the portion of the elongated anode nearest the cathode has a lower level of impedance to the nerve than does another portion of the elongated anode, further from the cathode. For some applications, the variation in impedance is achieved by applying a coating (e.g., IrO2 or a more resistive material) in progressively increasing thickness to the elongated anode, beginning with a low level of the coating at the end of the elongated anode near the cathode. Alternatively or additionally, the geometry of the elongated anode is configured so as to effect the change in impedance as described. It is noted that the impedance between any site on the elongated anode and the nerve is a function not only of the properties of the anode itself, but also of the biological material which naturally permeates the region between the nerve and the anode.

For some applications, a primary fiber-selection anode is incorporated into the housing, adjacent to the cathode and on the other side of the housing from the primary and secondary inhibiting anodes. (Thus, the sequence of electrodes in the housing is: primary fiber-selection anode, cathode, primary inhibiting anode, secondary inhibiting anode.) The primary fiber-selection anode is preferably driven to apply anodal current of sufficient magnitude to block cathode-induced action potential propagation in some fibers, generally the larger fibers, which are more sensitive to the anodal current. If the current applied by the primary fiber-selection anode is not too high, then less-sensitive fibers, typically the smaller fibers in the nerve, are not blocked by the anodal current. Therefore, action potentials induced by the cathode continue to propagate in the smaller fibers, past the primary fiber-selection anode and out of the housing. By increasing the current driven through the primary fiber-selection anode, progressively smaller fibers are inhibited from propagating action potentials. Conversely, by decreasing the application of current through the primary fiber-selection anode, larger fibers are able to propagate action potentials, until, in the limit where the primary fiber-selection anode's current is zero, all fibers stimulated by the cathode convey their action potentials out of the housing and towards the target.

In a preferred embodiment, a secondary fiber-selection anode is also incorporated into the housing, adjacent to the primary fiber-selection anode and on the far side of the cathode. (Thus, the sequence of electrodes in the housing is: secondary fiber-selection anode, primary fiber-selection anode, cathode, primary inhibiting anode, secondary inhibiting anode.) In a fashion analogous to that described hereinabove with respect to the secondary inhibiting anode, the secondary fiber-selection anode is preferably driven to apply a current to the nerve smaller than that applied by the primary fiber-selection anode, so as to counteract the virtual cathode effect which would otherwise, in some circumstances, induce action potential propagation responsive to the current applied by the primary fiber-selection anode.

In preferred embodiments of the present invention, an electrode assembly for applying current to a nerve having a longitudinal axis comprises a housing, adapted to be placed in a vicinity of the nerve and a cathode and an anode, fixed to the housing. The cathode and anode are attached to the housing such that, when the housing is placed in the vicinity of the nerve, both the distance of the cathode and the distance of the anode to the axis are at least approximately 1.5 times greater than the radius of the nerve. By placing the cathode and anode at such a distance, increased electrical field uniformity is obtained within the nerve. In particular, the activation function (as defined in the Background section of this application) varies only relatively little across the cross-section of the nerve. This, in turn, increases the ability of a control unit driving the cathode and anode to assure that most fibers within the nerve will experience generally the same level of applied currents.

In preferred embodiments of the present invention, an electrode assembly is provided for applying current to a nerve having a radius and a longitudinal central axis. The electrode assembly comprises a housing, which is placed in a vicinity of the nerve, and first and second electrodes, fixed to the housing. An insulating element is fixed to the housing between the first and second electrodes so as to define a characteristic closest "insulating element distance" to the central axis that is at least approximately 1.5 times greater than the radius of the nerve. Typically, the electrodes are located at the same distance from the central axis or at a greater distance therefrom. In a preferred embodiment, the face of each electrode is located at a distance from the central axis less than or equal to the closest insulating element distance plus the width (i.e., the longitudinal extent along the nerve) of the electrode. In a preferred embodiment, the width of each electrode is approximately one half of the radius of the nerve.

Although many geometrical configurations are suitable for applying the principles of the present invention, the housings, electrodes, and insulating elements described herein are typically generally cylindrical, i.e., having circular cross-sections. Alternatively or additionally, at least some of these components are located at discrete locations with respect to the axis of the nerve (e.g., a single electrode located at "12 o'clock," or four electrodes or insulating elements may be evenly distributed around the axis).

In preferred embodiments of the present invention, an electrode assembly for applying current to a nerve comprises a cathode and a plurality of anodes. The cathode is placed in a vicinity of a cathodic site of the nerve, and the plurality of anodes are placed in a vicinity of respective anodal longitudinal sites of the nerve. The plurality of anodes apply respective anodal currents to the nerve, that define, in combination, an anodal activation function having a depolarization portion and a hyperpolarization portion. For many applications of the present invention, the hyperpolarization portion is the "desired" portion of the anodal activation function. For example, the hyperpolarization portion may be configured to block action potential propagation in a particular direction.

By contrast, it is desired when performing many of these applications to minimize the depolarization portion of the anodal activation function, because the location on the nerve of the depolarization portion corresponds to the location of the virtual cathode described hereinabove. If no countermeasures would be taken, the virtual cathode could be associated with an undesired stimulation of fibers in the nerve under the virtual cathode. The virtual cathode effect could be minimized to some extent by reducing the anodal current, but, if in excess, this would result in a decrease in the magnitude of the (typically desired) hyperpolarization region. If the anodal current is only minimally reduced, in order to avoid adversely decreasing the magnitude of the hyperpolarization region, then the virtual cathode effect would typically still be present. The inventors have determined that for many electrode configurations, there is no suitable balance, i.e., either the virtual cathode effect will be reduced to a desired level, or the hyperpolarization portion of the activation function will be maintained at a sufficiently high magnitude.

To address this issue, the plurality of anodes provided by these embodiments of the present invention are preferably configured so as to have the maximum magnitude of the hyperpolarization portion be at least five times greater than the maximum magnitude of the depolarization amplitude. In this manner, the desired hyperpolarization effect is preserved, and the extent of depolarization due to the anodal current is minimized. Preferably, this ratio of anodally-induced hyperpolarization to depolarization is attained by using one or more of the following: (a) one or more secondary inhibiting anodes, as described hereinabove, to minimize the virtual cathode effect, (b) one or more insulating elements whose closest approach to the nerve generally remains further from the central axis of the nerve than approximately 1.5 times the radius of the nerve, or (c) electrodes, whose closest approach to the nerve generally remains further from the central axis of the nerve than approximately 1.5 times the radius of the nerve.

In preferred embodiments of the present invention, an electrode assembly for applying current to a nerve having a longitudinal axis, comprises two or more electrodes, adapted to be placed in a vicinity of a longitudinal site of the nerve, at respective positions around the axis. If there are only two electrodes, then the control unit preferably alternates the direction of driving a current between the two electrodes at a rate greater than 1000 Hz.

When there are three or more electrodes, thereby defining a ring of electrodes, the control unit preferably cycles around the electrodes in accordance with a stimulation protocol. For example, one such protocol for three electrodes may include driving current between electrodes 1 and 2, then 2 and 3, then 3 and 1, then 1 and 2, etc., cycling through the combinations at an electrode-pair transition average rate of greater than 1000 Hz, or, for some applications, greater than 10,000 Hz. For larger numbers of electrodes, e.g., 6, 12, or 24, the stimulation cycling protocol is typically more complex, and is preferably configured to cause current to pass through or close to most or all fibers in the nerve at the longitudinal site where the ring of electrodes is placed. One such complex protocol includes effectively creating a star out of the current lines passing through the nerve, or ensuring that each electrode in the ring conveys current to some, most, or all of the other electrodes.

Advantageously, due to the very high application rate of the current from the different electrodes compared to the relatively-low biological response rate of the fibers within the nerve, the fibers at that longitudinal site are effectively all stimulated at substantially the same time. In this manner, a single wave of action potential propagation is initiated from the longitudinal site at substantially the same time, and can be subsequently manipulated at other sites on the nerve using techniques described herein or in one or more of the patent applications cited herein that are assigned to the assignee of the present patent application and are incorporated herein by reference. Further, unlike solid ring electrodes which surround the nerve and conduct a significant portion of their current outside of the nerve, directly to the anode or cathode adjacent thereto, a larger portion of the current is conveyed into the nerve itself using the stimulation protocols described herein. From the "perspective" of the nerve, which functions at rates considerably slower than the switching rate of the ring of electrodes, it is as if a large portion of its nerve fibers were simultaneously stimulated.

In preferred embodiments of the present invention, an electrode assembly for applying current to a nerve having a longitudinal axis comprises a ring of two or more cathodes and a ring of two or more anodes, each ring of electrodes adapted to be placed around the nerve axis, at a respective cathodic or anodal longitudinal site of the nerve. Preferably, a control unit drives an anode in the ring of anodes to drive current through the nerve to a cathode typically at another orientation with respect to the axis, in order to stimulate fibers in the nerve nearer the cathode. Thus, for example, if each ring has twelve electrodes, then in one preferred stimulation protocol, the anode at "12 o'clock" with respect to the axis drives current generally through the nerve to the cathode at 6 o'clock. After a very short delay (typically 10-100 microseconds), the anode at 1 o'clock drives current generally through the nerve to the cathode at 7 o'clock. The pattern is preferably continued for all of the electrodes. It will be appreciated by one who has read the disclosure of the present patent application that a variety of stimulation protocols may be developed, and that a suitable protocol should typically be determined in accordance with the anatomy of the nerve, the types of nerve fibers therein, and the purpose of the stimulation, among other factors.

There is therefore provided, in accordance with a preferred embodiment of the present invention, apparatus for applying current to a nerve, including:

a cathode, adapted to be placed in a vicinity of a cathodic longitudinal site of the nerve and to apply a cathodic current to the nerve;

a primary inhibiting anode, adapted to be placed in a vicinity of a primary anodal longitudinal site of the nerve and to apply a primary anodal current to the nerve; and a secondary inhibiting anode, adapted to be placed in a vicinity of a secondary anodal longitudinal site of the nerve and to apply a secondary anodal current to the nerve, the secondary anodal longitudinal site being closer to the primary anodal longitudinal site than to the cathodic longitudinal site.

In a preferred embodiment, the apparatus is adapted to be placed on the nerve such that, relative to the anodal longitudinal sites, the cathodic longitudinal site is proximal to a brain of a subject, the subject including the nerve. Alternatively, the apparatus is adapted to be placed on the nerve such that, relative to the anodal longitudinal sites, the cathodic longitudinal site is distal to a brain of a subject, the subject including the nerve.

In a preferred embodiment, the primary inhibiting anode is adapted to apply the primary anodal current to the nerve so as to block propagation of action potentials past the primary anodal longitudinal site.

For some applications, the primary inhibiting anode is adapted to apply the primary anodal current to the nerve so as to block propagation past the primary anodal longitudinal site of action potentials in a first set of nerve fibers, and to allow propagation past the primary anodal longitudinal site of action potentials in a second set of nerve fibers, the second set of nerve fibers having characteristic diameters generally smaller than characteristic diameters of the nerve fibers in the first set.

In a preferred embodiment, the cathode includes a plurality of cathodes, placed in the vicinity of the cathodic longitudinal site of the nerve, at respective positions around an axis of the nerve. In this case, the plurality of cathodes are preferably adapted to apply the cathodic current at a characteristic frequency greater than 1000 Hz.

Preferably, the apparatus includes a primary insulating element disposed between the cathode and the primary inhibiting anode. The primary insulating element is typically disposed in a position with respect to the cathode and the primary inhibiting anode so as to guide the flow of current between the cathode and the primary inhibiting anode. For some applications, the apparatus includes a secondary insulating element, disposed between the primary inhibiting anode and the secondary inhibiting anode. In this case, a characteristic size of the secondary insulating element is preferably smaller than a characteristic size of the primary insulating element. Alternatively or additionally, a characteristic distance of the secondary insulating element to an axis of the nerve is greater than a characteristic distance of the primary insulating element to the axis of the nerve.

In some preferred embodiments, the apparatus includes a tertiary inhibiting electrode, adapted to be placed in a vicinity of a tertiary anodal longitudinal site of the nerve and to apply a tertiary anodal current to the nerve, the tertiary anodal longitudinal site being closer to the secondary anodal longitudinal site than to the primary anodal longitudinal site. In a preferred embodiment, the tertiary inhibiting anode is configured such that a current density of the tertiary anodal current is of lower magnitude than a magnitude of a current density of the secondary anodal current.

Preferably, the apparatus includes a housing, coupled to the cathode, the primary inhibiting anode and the secondary inhibiting anode, adapted to facilitate placement of the cathode and the anodes in the vicinities of their respective sites. In a preferred embodiment, the housing is configured such that an arc, defined by an extent that the housing is adapted to surround the nerve, is between about 90 and 270 degrees. Alternatively, the housing is configured such that an arc, defined by an extent that the housing is adapted to surround the nerve, is between about 270 and 359 degrees.

Typically, a closest cathode distance to an axis of the nerve, a closest primary inhibiting anode distance to the axis, and a closest secondary inhibiting anode distance to the axis are all at least approximately 1.5 times greater than the radius of the nerve.

For some applications, the secondary inhibiting anode is configured such that a secondary anodal current density induced by the secondary anodal current is of lower magnitude than a magnitude of a primary anodal current density induced by the primary anodal current. In a preferred embodiment, the primary anodal current is substantially of the same magnitude as the secondary anodal current. In a preferred embodiment, a characteristic surface area of the secondary inhibiting anode is higher than a characteristic surface area of the primary inhibiting anode. For example, the characteristic surface area of the secondary inhibiting anode may be at least 2 times higher than the characteristic surface area of the primary inhibiting anode.

In a preferred embodiment, the secondary inhibiting anode is configured such that a current density of the secondary anodal current is of lower magnitude than a magnitude of a current density of the primary anodal current. In this case, a characteristic surface area of the primary inhibiting anode may be higher than a characteristic surface area of the secondary inhibiting anode, and a common voltage may be applied to the primary inhibiting anode and to the secondary inhibiting anode.

For some applications:
(a) the primary inhibiting anode is adapted to have associated therewith a primary level of electrical impedance between the primary inhibiting anode and the nerve, when in the vicinity of the primary anodal longitudinal site, and
(b) the secondary inhibiting anode is adapted to have associated therewith a secondary level of electrical impedance between the secondary inhibiting anode and the nerve when in the vicinity of the secondary anodal longitudinal site, the secondary level of impedance having a higher magnitude than the primary level of impedance.

In a preferred embodiment, the secondary inhibiting anode is adapted to be coupled to the housing so as to define a secondary anode distance to an axis of the nerve, and wherein the primary inhibiting anode is adapted to be coupled to the housing so as to define a primary anode distance to the axis of the nerve that is smaller than the secondary anode distance. For example, a ratio of the secondary anode distance to the primary anode distance may be greater than approximately 1.5:1.

In a preferred embodiment, the apparatus includes a primary fiber-selection anode, adapted to be placed in a vicinity of a primary fiber-selection anodal longitudinal site of the nerve that is closer to the cathodic longitudinal site than to the primary anodal longitudinal site. For example, the apparatus may include a secondary fiber-selection anode, adapted to be placed in a vicinity of a secondary fiber-selection anodal longitudinal site of the nerve that is closer to the primary fiber-selection anodal longitudinal site than to the cathodic longitudinal site.

Preferably, the apparatus includes a control unit, adapted to drive the cathode to apply the cathodic current to the nerve, adapted to drive the primary inhibiting anode to apply the primary anodal current to the nerve, and adapted to drive the secondary inhibiting anode to apply the secondary anodal current to the nerve. In one preferred embodiment, the apparatus includes a first resistive element coupled between the control unit and the primary inhibiting anode, and a second resistive element coupled between the control unit and the secondary inhibiting anode, the second resistive element having a resistance higher than a resistance of the first resistive element.

For some applications, the apparatus includes exactly one lead that leaves the control unit for coupling the control unit to the primary and secondary inhibiting anodes. Alternatively, the apparatus includes respective leads that leave the control unit and couple the control unit to the primary and secondary inhibiting anodes.

The control unit is typically adapted to configure a current density of the secondary anodal current to be of lower magnitude than a current density of the primary anodal current. In a preferred embodiment, the control unit is adapted to configure an amplitude of a current density of the cathodic current to be between 1.1 and 2 times greater than an amplitude of a current density of the primary anodal current. Alternatively or additionally, the control unit is adapted to configure an amplitude of a current density of the cathodic current to be between 3 and 6 times greater than an amplitude of a current density of the secondary anodal current. Further alternatively or additionally, the control unit is adapted to configure an amplitude of a current density of the primary anodal current to be at least 2 times greater than an amplitude of a current density of the secondary anodal current.

There is also provided, in accordance with a preferred embodiment of the present invention, apparatus for applying current to a nerve having a radius and a longitudinal central axis, including:
a housing, adapted to be placed in a vicinity of the nerve; and
a cathode and an anode, fixed to the housing so as to define, when the housing is placed in the vicinity of the nerve, respective closest cathode and anode distances to the axis that are both at least approximately 1.5 times greater than the radius of the nerve.

Preferably, the closest cathode and anode distances to the axis are both at least approximately 2 times greater than the radius of the nerve.

In a preferred embodiment, the cathode includes a plurality of cathodes, placed in the vicinity of the cathodic longitudinal site of the nerve, at respective positions around the axis of the nerve, each of the respective positions being at a distance from the axis at least 1.5 times greater than the radius of the nerve.

In a preferred embodiment, the apparatus includes an insulating element disposed between the cathode and the anode. A characteristic distance of the insulating element to the axis of the nerve is typically at least 1.5 times greater than the radius of the nerve. For some applications, the distance of the anode to the axis is substantially the same as a characteristic distance of the insulating element to the axis of the nerve. For other applications, the distance of the anode to the axis is greater than a characteristic distance of the insulating element to the axis of the nerve. For example, the distance of the anode to the axis may be within 30% of the characteristic distance of the insulating element to the axis of the nerve plus a width of the anode.

There is further provided, in accordance with a preferred embodiment of the present invention, apparatus for applying current to a nerve having a radius and a longitudinal central axis, including:

a housing, adapted to be placed in a vicinity of the nerve;

first and second electrodes, fixed to the housing; and an insulating element, fixed to the housing between the first and second electrodes so as to define a characteristic closest insulating element distance to the central axis that is at least approximately 1.5 times greater than the radius of the nerve.

In a preferred embodiment, the insulating element is adapted to be placed in the vicinity of the nerve at a longitudinal site that is between respective longitudinal sites of the first and second electrodes. Alternatively, the insulating element is adapted to be placed in the vicinity of the nerve at a site with respect to the axis of the nerve that is between respective sites of the first and second electrodes, with respect to the axis.

There is still further provided, in accordance with a preferred embodiment of the present invention, apparatus for applying current to a nerve, including:

a cathode, adapted to be placed in a vicinity of a cathodic site of the nerve; and a plurality of anodes, adapted to be placed in a vicinity of respective anodal longitudinal sites of the nerve and to apply respective anodal currents to the nerve, that define, in combination, an anodal activation function having: (a) a hyperpolarizing portion thereof having a maximum hyperpolarizing amplitude, and (b) a depolarizing portion thereof, having a maximum depolarizing amplitude corresponding to a depolarizing site on the nerve distal with respect to the cathode to a site corresponding to the hyperpolarizing portion, wherein the maximum hyperpolarizing amplitude is at least five times greater than the maximum depolarizing amplitude.

In a preferred embodiment, the apparatus includes a housing to which the cathode and the plurality of anodes are coupled, wherein a distance of a first one of the anodes to an axis of the nerve is less than a distance of a second one of the anodes to the axis, the first one of the anodes being coupled to the housing closer to the cathode than the second one of the anodes.

Alternatively or additionally, the apparatus includes a housing to which the cathode and the plurality of anodes are coupled, wherein a surface area of a first one of the anodes is less than a surface area of a second one of the anodes, the first one of the anodes being coupled to the housing closer to the cathode than the second one of the anodes.

Preferably, the apparatus includes a housing to which the cathode and the plurality of anodes are coupled, and one of the anodes is positioned within the housing so as to reduce a virtual cathode effect induced by another one of the anodes.

The cathode and anodes are typically disposed such that a first one of the anodal longitudinal sites is between the cathodic site and a second one of the anodal longitudinal sites. In a preferred embodiment, the anodes are disposed such that the second one of the anodal longitudinal sites is between the first one of the anodal longitudinal sites and a third one of the anodal longitudinal sites. Preferably, the anodes are adapted such that a current density of the anodal current applied at the second one of the anodal longitudinal sites has a lower magnitude than a magnitude of a current density of the anodal current applied at the first one of the anodal longitudinal sites.

For some applications, the anodes are adapted such that a ratio of the current density of the anodal current applied at the first site to the current density of the anodal current applied at the second site is at least 2:1. Preferably, the anodes are adapted such that a ratio of the current density of the anodal current applied at the first site to the current density of the anodal current applied at the second site is at least 5:1.

There is yet further provided, in accordance with a preferred embodiment of the present invention, apparatus for applying current to a nerve, including:

a cathode, adapted to be placed in a vicinity of a first longitudinal site of the nerve; and an elongated anode, adapted to be placed in a vicinity of a second longitudinal site of the nerve, and, when so placed, to have associated therewith: (a) a first level of electrical impedance between the nerve and a location on the elongated anode proximal to the cathode, and (b) a second level of electrical impedance, greater than the first level, between the nerve and a location on the elongated anode distal to the cathode.

Preferably, the apparatus includes a coating disposed on a surface of the elongated anode, configured to provide the first and second levels of impedance. In a preferred embodiment, the coating is disposed on the surface in different respective thicknesses at the two locations on the elongated anode. Alternatively or additionally, the coating includes a coating that has undergone a surface treatment, and wherein the coating is configured to provide the first and second levels of impedance responsive to having undergone the surface treatment. In a preferred embodiment, the coating includes iridium oxide, titanium nitrite, and/or platinum iridium.

There is also provided, in accordance with a preferred embodiment of the present invention, apparatus for applying current to a nerve having a longitudinal axis, including:

two or more electrodes, adapted to be placed in a vicinity of a longitudinal site of the nerve, at respective positions around the axis; and a control unit, adapted to:

(a) drive current between two of the electrodes, thereby defining a first pair of the electrodes and a first direction of current flow, and, less than one millisecond later, (b) drive current between two of the electrodes, thereby defining a second pair of the electrodes and a second direction of current flow, and (c) cycle between steps (a) and (b) at a rate greater than 1000 Hz, wherein at least either the first pair of electrodes is different from the second pair of electrodes or the first direction of current flow is different from the second direction of current flow.

Typically, the two or more electrodes include three or more electrodes, or four or more electrodes.

For some applications, the control unit is adapted to set the rate to be greater than 4000 Hz.

There is yet additionally provided, in accordance with a preferred embodiment of the present invention, apparatus for applying current to a nerve having a longitudinal axis, including:

a set of two or more cathodes, adapted to be placed in a vicinity of a cathodic longitudinal site of the nerve, at respective positions around the axis; and a set of two or more anodes, adapted to be placed in a vicinity of an anodal longitudinal site of the nerve, at respective positions around the axis.

As appropriate, the two or more cathodes may include six or more cathodes, e.g., twelve or more cathodes.

The apparatus typically includes a control unit, adapted to drive current between respective ones of the cathodes and respective ones of the anodes. The control unit is preferably adapted to cycle the current driving at a rate greater than 1000 Hz. In a preferred embodiment, the control unit is adapted to complete a sweep of driving the current through substantially all of the cathodes in less than 1000 microseconds. Preferably, the control unit is adapted to complete a sweep of driving the current through substantially all of the cathodes in less than 100 microseconds.

There is still additionally provided, in accordance with a preferred embodiment of the present invention, a method for applying current to a nerve, including:

applying cathodic current in a vicinity of a cathodic longitudinal site of the nerve;

applying a primary anodal current to the nerve in a vicinity of a primary anodal longitudinal site of the nerve; and applying a secondary anodal current to the nerve in a vicinity of a secondary anodal longitudinal site of the nerve that is closer to the primary anodal longitudinal site than to the cathodic longitudinal site.

There is yet additionally provided, in accordance with a preferred embodiment of the present invention, a method for applying current to a nerve having a radius and a longitudinal central axis, including applying cathodic and anodal current to the nerve from respective cathodic and anodal current-application sites that are both located at distances from the axis of the nerve which are at least approximately 1.5 times greater than the radius of the nerve.

There is also provided, in accordance with a preferred embodiment of the present invention, a method for applying current to a nerve, including:

applying cathodic current in a vicinity of a cathodic site of the nerve; and applying anodal currents in a vicinity of respective anodal longitudinal sites of the nerve, the currents defining, in combination, an anodal activation function having: (a) a hyperpolarizing portion thereof having a maximum hyperpolarizing amplitude, and (b) a depolarizing portion thereof, having a maximum depolarizing amplitude corresponding to a depolarizing site on the nerve distal, with respect to the cathodic site, to a site corresponding to the hyperpolarizing portion, wherein the maximum hyperpolarizing amplitude is at least five times greater than the maximum depolarizing amplitude.

There is further provided, in accordance with a preferred embodiment of the present invention, a method for applying current to a nerve having a longitudinal axis, including driving current between: (a) a set of two or more cathodic sites in a vicinity of a first longitudinal site of the nerve, which are located at respective positions around the axis, and (b) a set of two or more anodal sites in a vicinity of a second longitudinal site of the nerve, which are located at respective positions around the axis.

The present invention will be more fully understood from the following detailed description of the preferred embodiments thereof, taken together with the drawings, in which:

DETAILED DESCRIPTION OF PREFERRED EMBODIMENTS

Figure 1A:
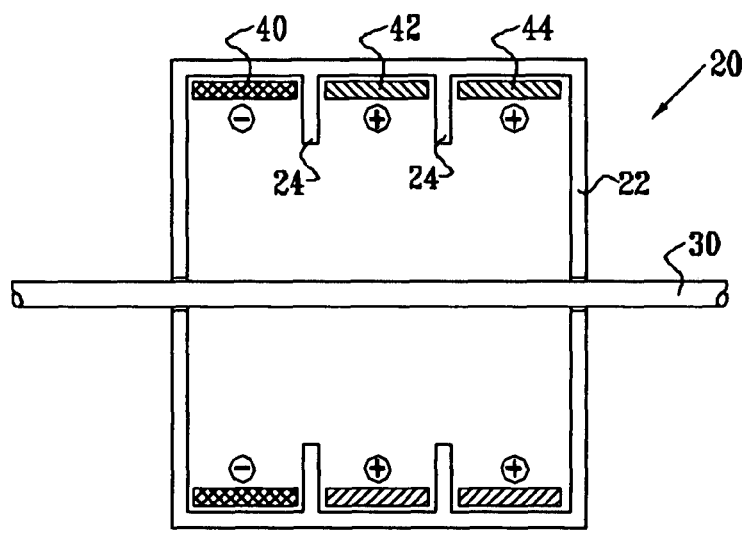
FIG. 1A is a schematic, cross-sectional illustration of an electrode assembly for applying current to a nerve, in accordance with a preferred embodiment of the present invention.
Figure 1B:
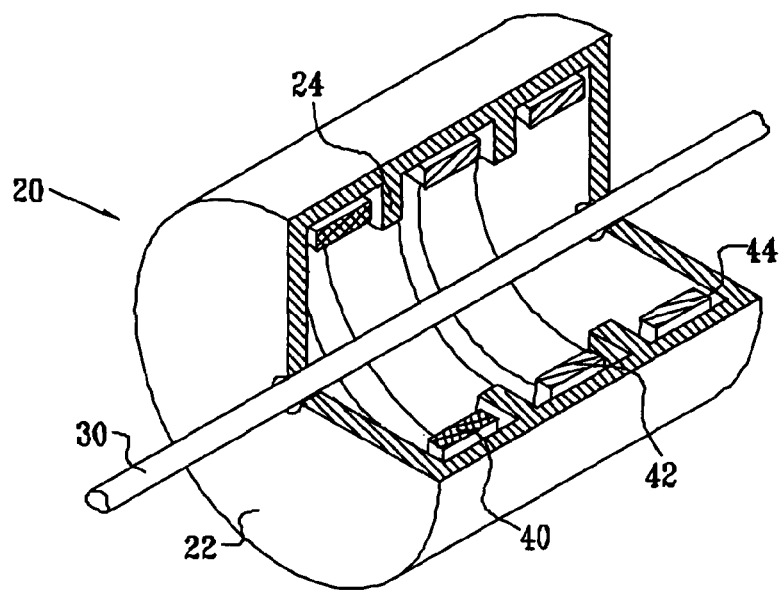
FIG. 1B is a schematic pictorial illustration of the electrode assembly of FIG. 1A, in accordance with a preferred embodiment of the present invention.

Reference is now made to FIGS. 1A and 1B. FIG. 1A is a schematic, cross-sectional illustration of an electrode assembly 20 for applying current to a nerve 30, in accordance with a preferred embodiment of the present invention. FIG. 1B is a schematic pictorial illustration of electrode assembly 20, in accordance with a preferred embodiment of the present invention. It is noted that although the various electrode assemblies shown in the figures generally contain cylindrical configurations of their elements, other geometrical configurations, such as non-rotationally symmetric configurations, are also suitable for applying the principles of the present invention. In particular, a housing 22 of the electrode assembly (and the electrodes themselves) may form a complete circle around the nerve, or it may define an arc between approximately 0 and 90 degrees, between 90 and 180 degrees, between 180 and 350 degrees, or between 350 and 359 degrees around the nerve. (One such preferred embodiment, shown in FIG. 1B, includes the housing and the electrodes defining an arc of 270 degrees.)

Preferably, electrode assembly comprises a cathode 40, a primary inhibiting anode 42, and a secondary inhibiting anode 44. Each of these electrodes is fixed within housing 22 of the electrode assembly. Insulating elements 24, which are typically either part of the body of the housing or affixed thereto, are preferably placed so as to separate the electrodes, and to guide current from one of the electrodes towards the nerve prior to being taken up by another one of the electrodes. Preferably (as shown), the insulating elements are closer to nerve 30 than are the electrodes. Alternatively (not shown), insulating elements 24 are generally flush with the faces of the electrodes.

Typically, cathodic current driven through cathode 40 by a control unit (not shown) stimulates fibers within nerve 30 to generate action potentials which travel in both directions within the nerve—i.e., towards anodes 42 and 44 ("the anodal direction"), and in the opposite direction, out of housing 22, towards a target ("the target direction"). Anodal current driven through anode 42, by contrast, is typically applied so as to inhibit the action potentials which were induced by the cathodic current, and which subsequently traveled in the anodal direction.

For most applications, current applied by secondary inhibiting anode 44 is of lower magnitude than the current applied by primary inhibiting anode 42. In this manner, the "virtual cathode" effect induced by the primary anodal current is minimized. In accordance with a preferred embodiment of the present invention, application of the primary and secondary anodal currents in appropriate ratios is configured to generally minimize the virtual cathode effect. Typically, but not necessarily, the ratio of the primary to the secondary anodal current ranges from 2:1 to 10:1.

Figure 2A:
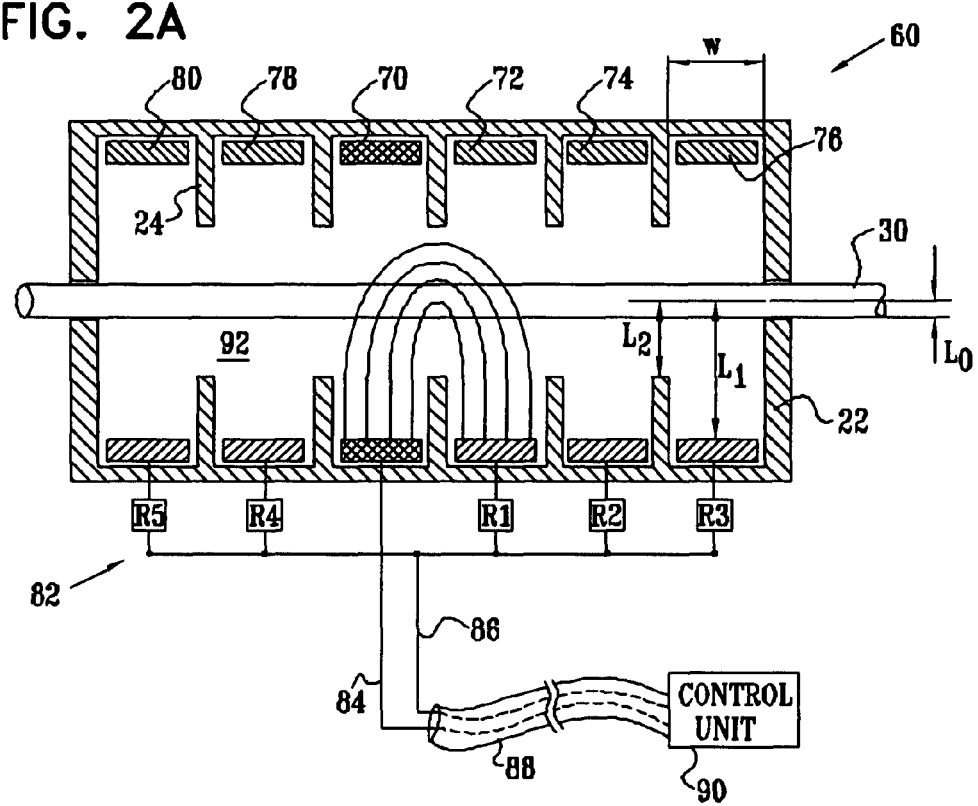
FIGS. 2A and 2B are schematic, cross-sectional illustrations of other electrode assemblies for applying current to a nerve, in accordance with respective preferred embodiments of the present invention.

FIG. 2A is a schematic, cross-sectional illustration of an electrode assembly 60, in accordance with another preferred embodiment of the present invention. Electrode assembly 60 comprises a cathode 70, a primary inhibiting anode 72, and a secondary inhibiting anode 74, which are typically driven in a manner analogous to that described hereinabove with respect to cathode 40 and primary and secondary inhibiting anodes 42 and 44.

Preferably, electrode assembly 60 additionally comprises a tertiary anode 76, which is employed to reduce any virtual cathode effect which may be induced by secondary inhibiting anode 74. For example, relative to a normalized cathodic current of −1, the primary inhibiting anode, secondary inhibiting anode, and tertiary anode may be configured to apply respective currents of 0.66, 0.25, and 0.09. Typically, the magnitude of the current from the tertiary anode is sufficiently small, such that the virtual cathode effect resulting therefrom does not generate action potentials that interfere with the performance of electrode assembly 60. For some applications, however, particularly when the current from primary inhibiting anode 72 is relatively high, additional anodes (not shown) are provided in electrode assembly 60.

Electrode assembly 60 preferably comprises a primary fiber-selection anode 78, adjacent to cathode 70 and on the other side of the housing from anodes 72, 74, and 76. The current applied by cathode 70 typically induces bi-directional action potential propagation in fibers in nerve 30 having a range of diameters. In order to block propagation past anode 78 of those action potentials traveling in relatively larger fibers, the primary fiber-selection anode is preferably driven to apply anodal current configured to block action potential propagation in these larger fibers of nerve 30, and configured not to block action potential propagation in the smaller fibers. In particular, since the larger fibers are generally more sensitive to being blocked by a lower level of anodal current than are the smaller fibers, a given level of current applied through fiber-selection anode 78 typically blocks action potentials in the larger fibers, while allowing passage of action potentials induced by the current from cathode 70 and traveling in the small fibers. Therefore, action potentials induced by the cathode continue to propagate in the smaller fibers, past primary fiber-selection anode 78, out of housing 22, and towards a target site. By increasing the current driven through the primary fiber-selection anode, progressively smaller fibers are inhibited from propagating action potentials. Conversely, by decreasing the application of current through primary fiber-selection anode 78, larger fibers are able to propagate action potentials.

For applications in which the current applied through primary fiber-selection anode 78 is sufficient to create a substantial virtual cathode effect, a secondary fiber-selection anode 80 is preferably incorporated into electrode assembly 60, adjacent to the primary fiber-selection anode and on the far side of cathode 70. In a fashion analogous to that described hereinabove with respect to secondary inhibiting anode 74, secondary fiber-selection anode 80 is preferably driven to apply a current to the nerve smaller than that applied by primary fiber-selection anode 78, so as to counteract the virtual cathode effect which would otherwise, in some circumstances, induce action potential propagation responsive to the current applied by primary fiber-selection anode 78.

Preferably, fixed ratios for the currents applied by anodes 72, 74, 76, 78, and 80 are pre-defined and are set in hardware, e.g., by a set 82 of resistors R1, R2, R3, R4, and R5, which couple a single lead 86 coming from a control unit 90 to the respective anodes. Typically, a guide tube 88 conveys lead 86, in combination with a second lead 84 that drives cathode 70, from control unit 90 to electrode assembly 60. Advantageously, this embodiment provides control over multiple anodes, and corresponding reduction of the virtual cathode effect, with a minimum number of leads.

Alternatively, for some applications (not shown), particularly when cathodic and anodal current parameters vary over a wide range, the various anodes are independently driven by the control unit via respective leads, so as to optimize the minimization of the virtual cathode effect and the maximization (when appropriate) of anodally-induced hyperpolarization. For some applications, a combination of the two techniques described are utilized, whereby, for example, anodes 72, 74, and 76 are driven by current in a single lead, and anodes 78 and 80 are driven by current in two additional, separate leads.

Preferably, electrode assembly 60 (as well as the other electrode assemblies described herein, as appropriate) has physical dimensions configured so as to provide a relatively uniform activation function across the cross-section of nerve 30. The distance L1 separating the central longitudinal axis of nerve 30 from cathode 70 and from anodes 72, 74, 76, 78, and 80 is typically at least approximately 1.5 times greater than the radius L0 of the nerve. For many applications, L1 is greater than two times L0. By placing the cathode and anodes at such distances, increased electrical field uniformity is obtained within the nerve, particularly as the gradients in the activation function are largest near the electrodes, and are significantly reduced across the cross-section of the nerve. This, in turn, increases the ability of control unit 90 to assure that most fibers within the nerve will experience generally the same level of applied currents.

Insulating elements 24 preferably separate cathode 70 from anodes 72 and 78. For some applications, additional insulating elements 24 separate the various adjacent anodes in electrode assembly 60. The insulating elements define a characteristic closest "insulating element distance" L2 to the axis of nerve 30 that is preferably at least approximately 1.5 times greater than L0. It will be appreciated that for structural reasons, spokes or other offshoots of the insulating elements may come closer to the nerve. However, the "functional" portions of the insulating elements, i.e., those portions which provide a substantial effect on the direction of current flow between the electrodes and through the nerve, preferably remain at a closest distance L2 of at least 1.5*L0. For some applications, particularly those in which battery life is a pressing factor, L2 is set to be less than 1.5*L0, at the expense of some uniformity of the applied field.

Typically, L1 is greater than or equal to L2. For anode and cathode widths w, preferred values for L1 are in the range L2<L1<1.5 (L2+w). Further preferably, L2+0.5w<L1<L2+w. Typically, the width w of the electrodes is approximately equal to 0.5*L0. (The width w, as well as other dimensions, are not drawn to scale in the figures.) In accordance with a preferred embodiment of the present invention, when L0 is between 1 and 2 mm, L2 is preferably between 1.5 and 3 mm, L1 is between 1.5 and 4 mm, and w is between 0.5 and 1 mm.

Figure 2B:
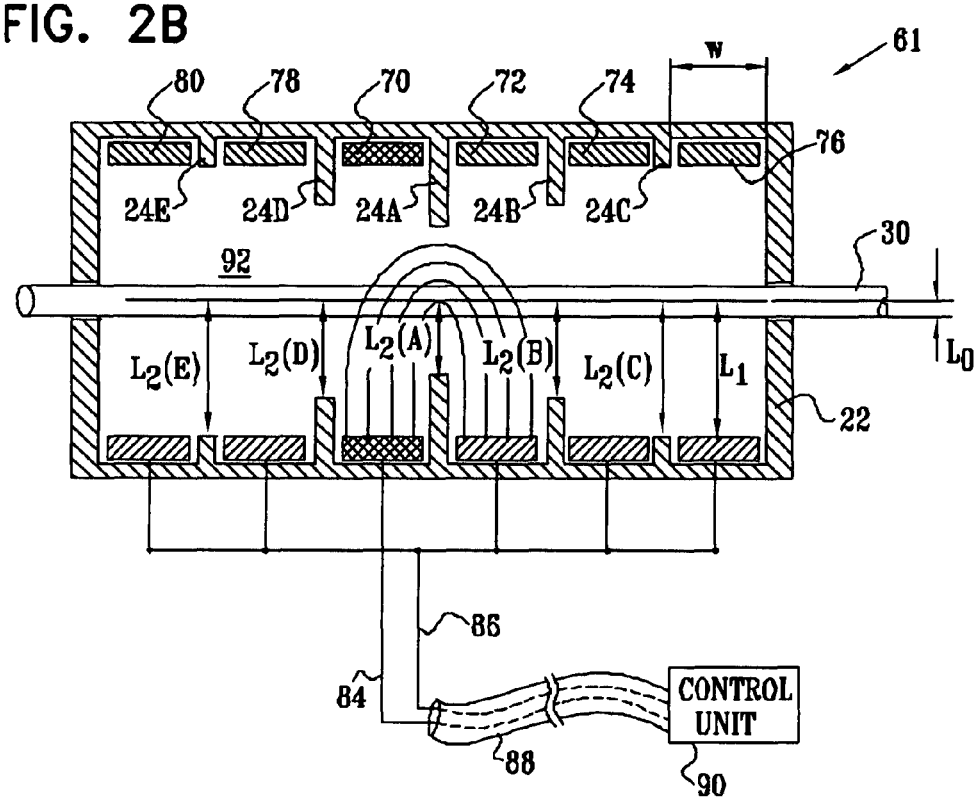

FIG. 2B is a schematic, cross-sectional illustration of an electrode assembly 61, in accordance with another preferred embodiment of the present invention. Electrode assembly 61 is generally similar to electrode assembly 60, described hereinabove with reference to FIG. 2A, except for differences as described.

Whereas in electrode assembly 60, insulating elements 24 all had generally equal dimensions, electrode assembly 61 provides each of five insulating elements 24A, 24B, 24C, 24D, and 24E with a respective (typically different) distance to the axis of nerve 30 of L2(A), L2(B), L2(C), L2(D), and L2(E). In general, as the distance L2(x) for any given one of the insulating elements decreases, the current density experienced by the nerve in a vicinity of the insulating element increases. Thus, for example, in the preferred embodiment shown in FIG. 2B, L2(C) corresponding to insulating element 24C is relatively large, such that the current density in the nerve near anode 76 is low.

Figure 3A:
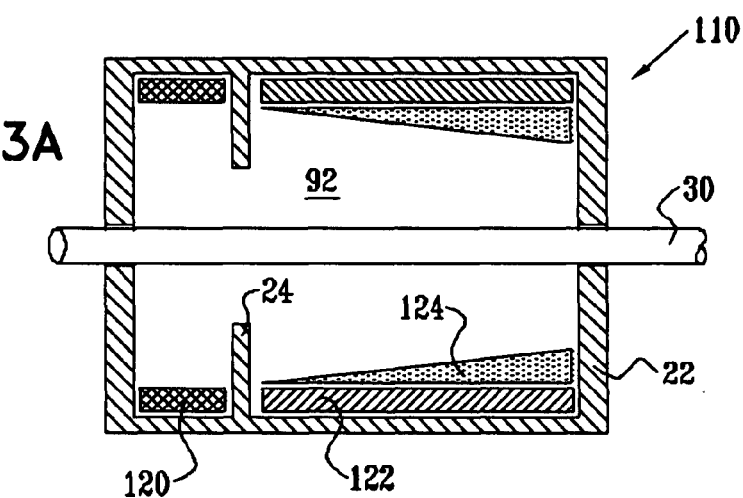
FIGS. 3A, 3B, and 3C are schematic, cross-sectional illustrations of yet other electrode assemblies for applying current to a nerve, in accordance with respective preferred embodiments of the present invention.

FIG. 3A is a schematic, cross-sectional illustration of an electrode assembly 110, in accordance with a preferred embodiment of the present invention. Electrode assembly 110 is analogous to electrode assembly 20, described hereinabove with reference to FIG. 1A, except for differences as described. A cathode 120 of electrode assembly 110 serves generally the same purpose as cathode 40, while an elongated anode 122 preferably replaces anodes 42 and 44. Typically, elongated anode 122 is 0.5 mm-10 mm in length, although it may be longer or shorter responsive to the level of currents expected to be applied therethrough.

Elongated anode 122, when placed on or over nerve 30, preferably has at least two levels of electrical impedance associated therewith, between respective sites on the elongated anode and the nerve. A biological material 92, typically including fibrous tissue and body fluids, generally occupies some of the space between the electrodes and the nerve. The impedance governing the passage of current from elongated anode 122 to nerve 30 is therefore typically a function of the properties of biological material 92. Additionally, a resistive element 124 (e.g., a shaped iridium oxide coating, a titanium nitride coating, or a platinum iridium coating) preferably provides greater electrical impedance distal to cathode 120 than proximal thereto. In a preferred embodiment, the coating undergoes a surface treatment (e.g., "sand blasting" or a chemical treatment), in which the effective microscopic surface area is increased by the treatment. Preferably, the proximal-to-the-cathode end of the coating is more heavily treated by the surface treatment, and therefore has lower impedance. Alternatively or additionally, the geometry of the elongated anode is configured so as to effect the change in impedance as described.

Typically, the anodal current leaving the portion of elongated anode 122 distal to cathode 120 minimizes the virtual cathode effect induced thereat by anodal current leaving the portion of elongated anode 122 proximal to cathode 120.

Figure 3B:
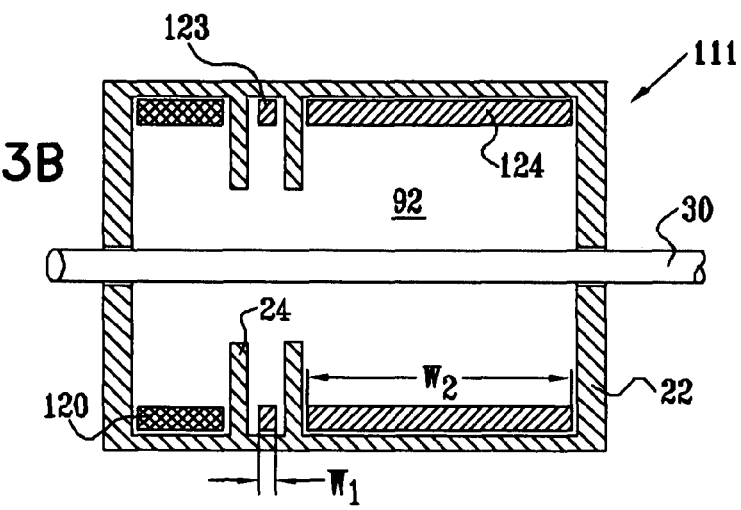

FIG. 3B is a schematic, cross-sectional illustration of an electrode assembly 111, in accordance with a preferred embodiment of the present invention. Preferably, a current density in a vicinity of a primary anode 123 is higher than a current density in a vicinity of a secondary anode 124. The difference in current densities is preferably attained by having a width w2 of anode 124 be at least 2-10 times higher than a corresponding width w1 of anode 123. In this manner, when generally the same current is passed through both anodes, the current density—and thus the hyperpolarizing effect on the activation function—is greater near anode 123 than near anode 124.

Figure 3C:
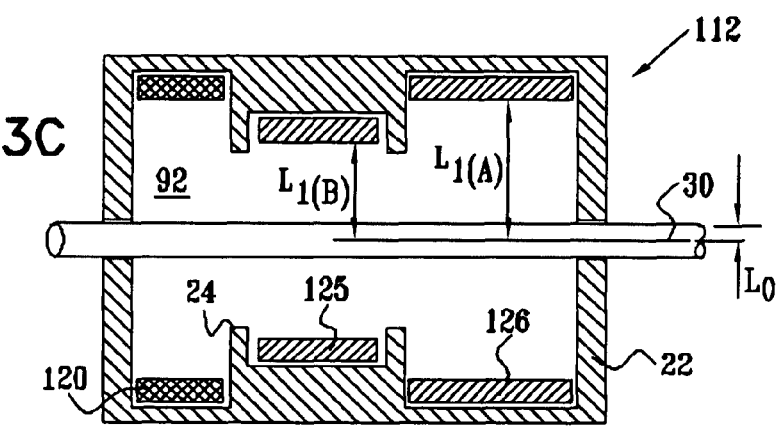

FIG. 3C is a schematic, cross-sectional illustration of an electrode assembly 112, in accordance with a preferred embodiment of the present invention. In this embodiment, the distance L1(B) between a primary anode 125 and the axis of nerve 30 is preferably smaller than the distance L1(A) between a secondary anode 126 and the axis of the nerve. The distance of cathode 120 from the axis is similar to L1(A) (as shown), while in other embodiments (not shown) the distance is closer to L1(B). In a manner similar to that described with reference to FIG. 3B, the geometrical configuration of the cathode and the anodes shown in FIG. 3C typically provides higher current density near the anode that is proximal to the cathode, and provides generally lower current density near the anode that is distal to the cathode.

Figure 4:
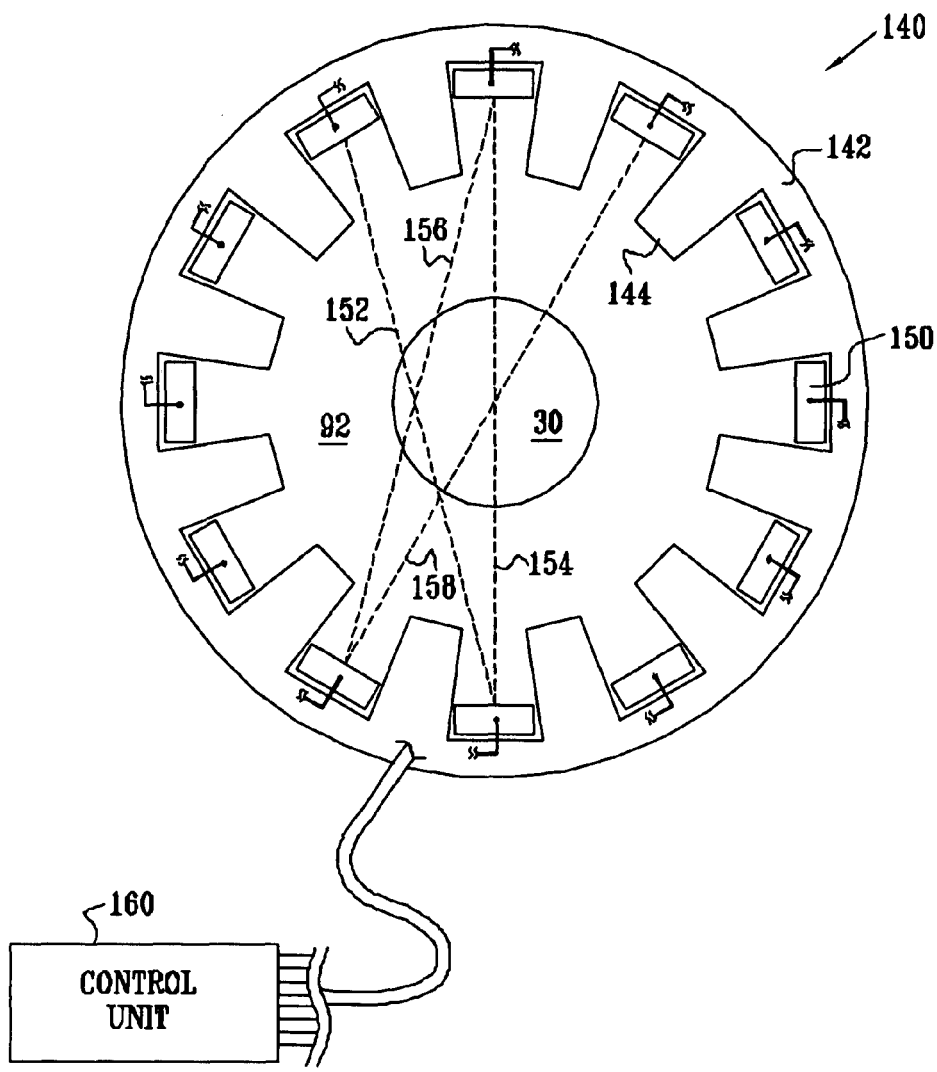
FIG. 4 is a schematic, cross-sectional illustration of still another electrode assembly for applying current to a nerve, in accordance with a preferred embodiment of the present invention.

FIG. 4 is a schematic, cross-sectional illustration of an electrode assembly 140 surrounding nerve 30, which is driven by a control unit 160 to apply current to the nerve, in accordance with a preferred embodiment of the present invention. Two or more electrodes 150 fixed to a housing 142 are placed at respective positions around the axis. Typically, electrodes 150 comprise at least three, and preferably four or more electrodes. In this case, insulating elements 144 are preferably disposed between adjacent electrodes. If there are only two electrodes, then control unit 160 preferably alternates the direction of the current driven between the two electrodes at a rate greater than 1000 Hz.

When there are three or more electrodes 150, thereby defining a ring of electrodes, control unit 160 preferably cycles its driving of the electrodes in accordance with a stimulation protocol. For example, one such protocol for three electrodes may include driving current between electrodes 1 and 2, then 2 and 3, then 3 and 1, then 1 and 2, etc., cycling through the combinations at an average rate of greater than 1000 Hz, or, for some applications, greater than 10,000 Hz. For larger numbers of electrodes, e.g., 6, 12, or 24, the stimulation cycling protocol is typically more complex, and is preferably configured to cause current to pass through or close to most or all fibers in the nerve at the longitudinal site where the ring of electrodes is placed. One such complex protocol includes effectively creating a star out of successive current lines passing through the nerve. In FIG. 4, an initial set of four such lines 152, 154, 156, and 158 are shown.

Figure 5:
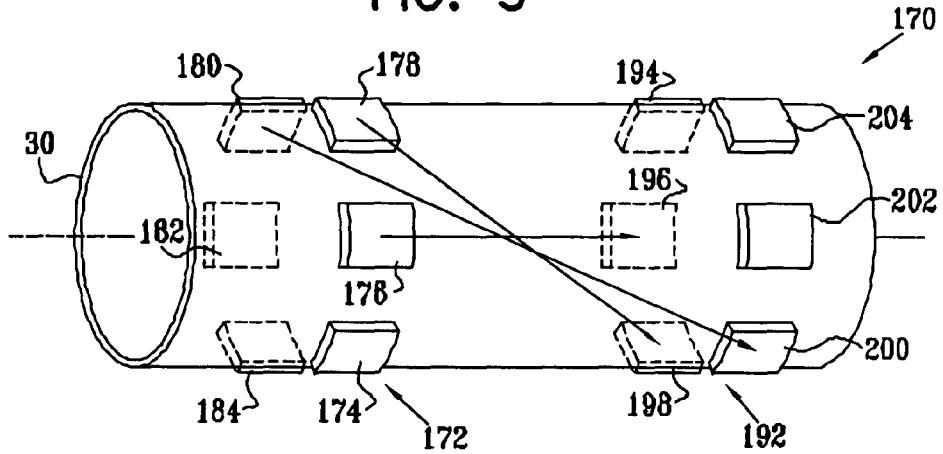
FIG. 5 is a schematic, pictorial illustration of an additional electrode assembly for applying current to a nerve, in accordance with a preferred embodiment of the present invention.

FIG. 5 is a schematic, pictorial illustration of an electrode assembly 170, in accordance with another preferred embodiment of the present invention. Electrode assembly 170 comprises an anodal ring 172 of two or more anodes and a cathodic ring 192 of two or more cathodes. In the preferred embodiment shown in FIG. 5, anodal ring 172 comprises anodes 174, 176, 178, 180, 182, and 184, and cathodic ring 192 comprises cathodes 194, 196, 198, 200, 202, and 204. Each ring of electrodes is placed around the nerve axis, at a respective anodal or cathodic longitudinal site of the nerve.

Preferably, a control unit drives anode 176 to drive current through nerve 30 to cathode 196, in order to initiate generation of action potentials near cathode 196 and/or near a substantial portion of cathodic ring 192. Cathode 196 and anode 176 are preferably at mutually-opposed orientations with respect to the axis. In this manner, a greater portion of the current from anode 176 enters nerve 30 than if, for example, the control unit were to drive anode 176 to send the same amount of charge to cathode 202. In this latter case, a substantial portion of the current leaving anode 176 would travel directly through the biological material surrounding nerve 30, and not enter into nerve 30.

In the example shown in FIG. 5, after anode 176 sends current to cathode 196, anode 178 sends current to cathode 198, and then anode 180 sends current to cathode 200. Preferably, an entire sweep of all of the electrodes in the two rings is accomplished within 0.01-1 millisecond.

Advantageously, by utilizing discrete electrodes arranged into a ring of cathodes and a ring of anodes, each located at respective longitudinal sites on the nerve, fibers in the nerve are stimulated near the ring of cathodes, and inhibited near the ring of anodes, typically using substantially less current than if a solid anode ring and a solid cathode ring were placed around the nerve. Further advantageously, steering of current to traverse or avoid certain regions in the cross-section of the nerve is readily attainable, using the techniques described herein, by suitable activation of the cathodes and/or anodes.

For simplicity, FIG. 5 shows only a single anodal ring 172. It is noted that the use of rings of anodes and/or a ring of cathodes is preferably also applied, as appropriate, in combination with the cathode—anode—anode configuration of FIGS. 1A and 1B, or in combination with the anode—anode—cathode—anode—anode—anode configuration of FIGS. 2A and 2B. In a preferred embodiment, some of the electrodes (e.g., cathode 70 and anodes 72 and 78) comprise multiple electrodes disposed in a ring, while others of the electrodes (e.g., anodes 74, 76, and 80) are generally solid rings, each comprising only a single ring.

Figure 6:
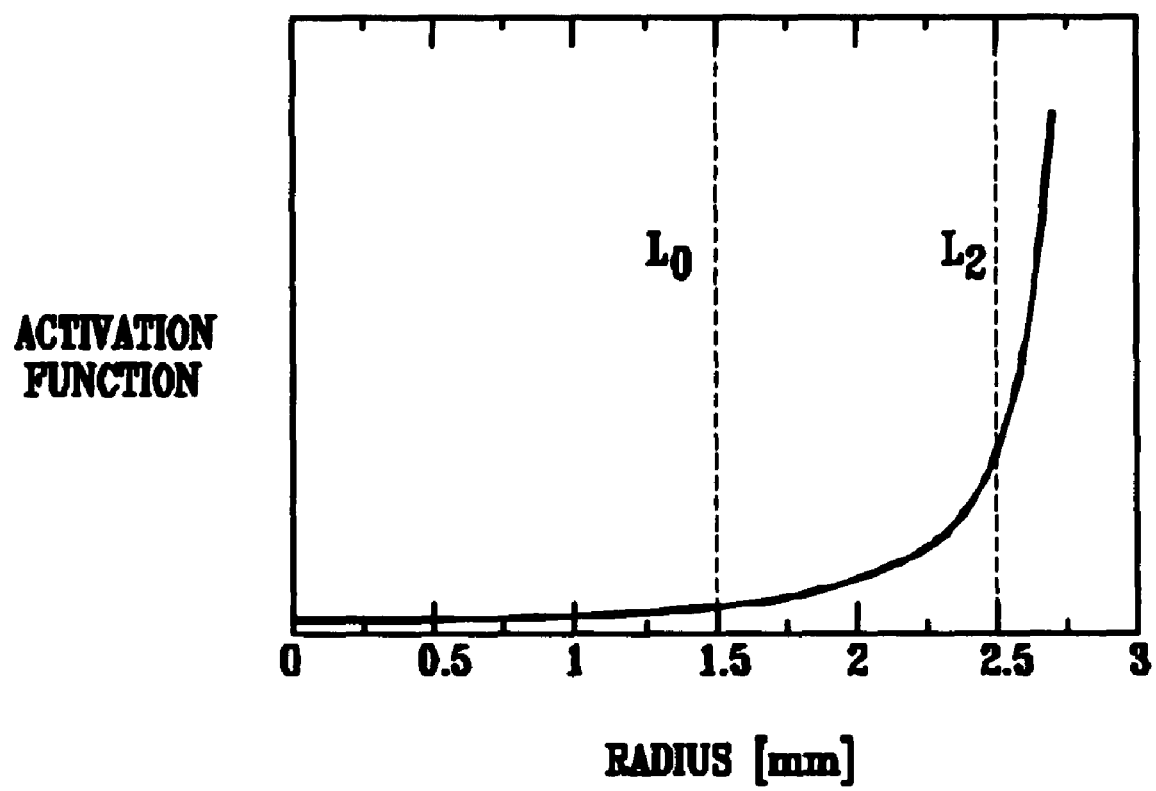
FIG. 6 is a graph modeling a calculated activation function over a range of distances from the central axis of a nerve to which current is applied using an electrode assembly such as that shown in FIG. 1A, in accordance with a preferred embodiment of the present invention.

FIG. 6 is a graph modeling calculated activation function over a range of distances from the central axis of a nerve, in accordance with a preferred embodiment of the present invention. The graph models, in a simplified fashion, the activation function, at a cathodic site, produced in response to application of current by, for example, electrode assembly 20 (FIG. 1A) or electrode assembly 60 (FIG. 2A). The equation producing the graph shown in FIG. 6 is:

$$AF(r) = \frac{I}{2\Pi} \int_0^{2\Pi} \left[1 + \left(\frac{r}{R}\right)^2 - 2\left(\frac{r}{R}\right)\cos\varphi\right]^{-1.5} d\varphi,$$

where r is the radius from the central axis of the nerve, and R is the distance of an electrode ring from the axis. L0 in the figure shows the radius of a typical nerve, and L2 shows the distance to an insulating element. As noted above, the amount of change of the activation function within the nerve (r<L0) is significantly smaller than the amount of change of the activation function outside the nerve (r>L0).

Figure 7:
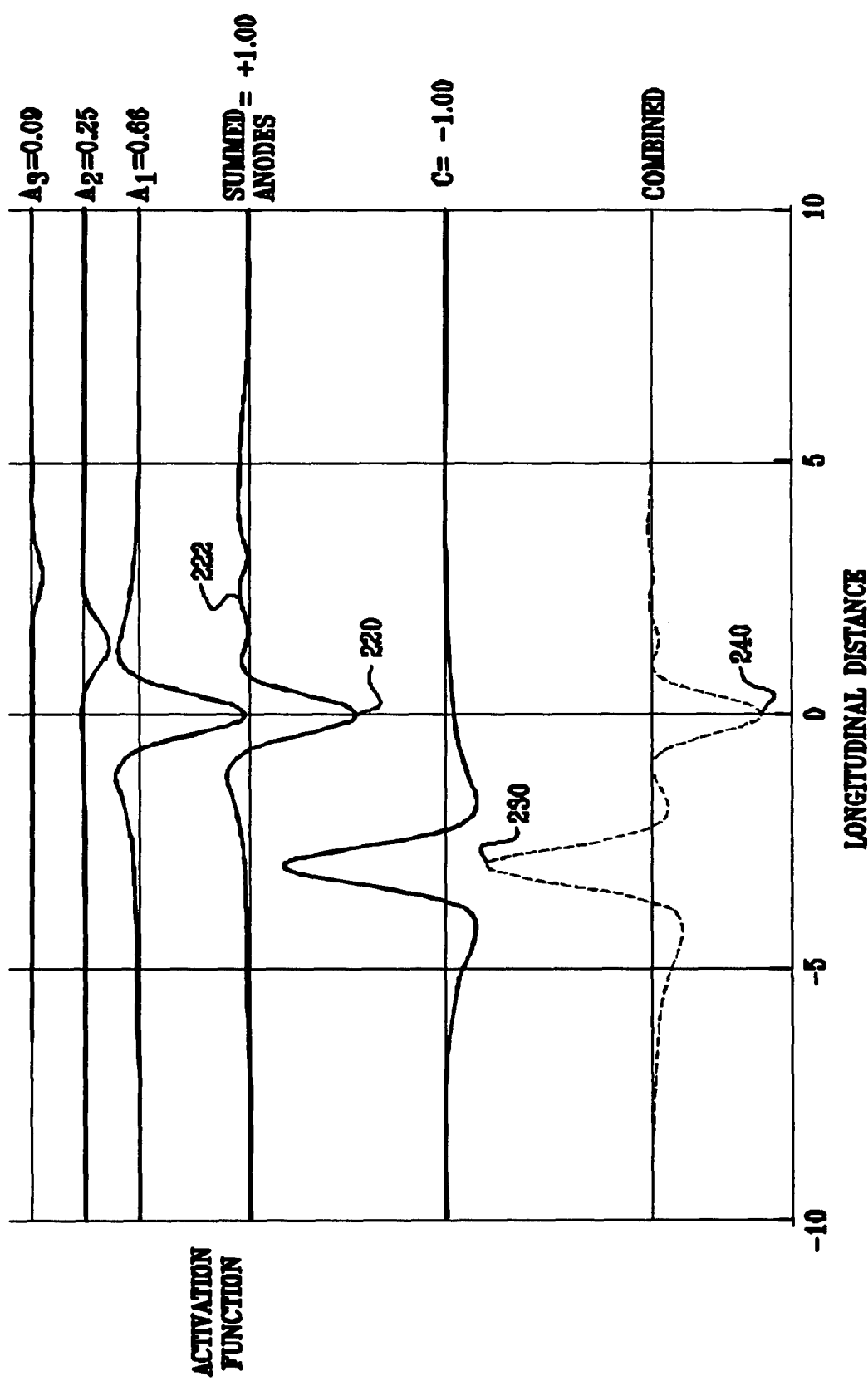
FIG. 7 is a graph modeling a calculated activation function over a portion of the length of a nerve to which current is applied using an electrode assembly such as that shown in FIG. 2A, in accordance with a preferred embodiment of the present invention.

FIG. 7 is a graph modeling calculated activation function over a portion of the length of nerve 30, when current is applied using an electrode assembly such as that shown in FIG. 2A (without applying current through anodes 78 and 80), in accordance with a preferred embodiment of the present invention. For the purposes of modeling the activation function, cathode 70 is placed at a longitudinal site on the nerve labeled z=−3 (in relative units), and anodes 72, 74, and 76 are placed at longitudinal positions z=0, 1.4, and 2.7. Anodes 72, 74, and 76 are driven to apply currents A1=0.66, A2=0.25, and A3=0.09, respectively. Each one of the electrodes generates its own activation function responsive to the applied currents, as modeled in FIG. 7.

The top three data lines in FIG. 7 show that each of the anodes generates a depolarization portion (most clearly seen for applied current A1) and a hyperpolarization portion (clearly seen for each anode). It is noted that the depolarization portion of the activation function generated by the largest applied anodal current (A1) at approximately z=1.2 is substantial, and, in many cases, is sufficient to stimulate fibers within the nerve.

The sum of the effect of each of the anodal activation functions is seen in the fourth data line in FIG. 7, labeled "summed anodes." This line demonstrates that the hyperpolarization portion of the activation function due to anodal current A2 significantly counteracts the depolarization portion of the activation function due to anodal current A1. Advantageously, the peaks 222 at z>0 are generally not of sufficient magnitude to excessively stimulate the nerve fibers within nerve 30 by means of the virtual cathode effect. Nevertheless, the maximum hyperpolarization peak 220 of the "summed anodes" curve remains strong, sufficient to inhibit action potential propagation in a substantial proportion of the fibers of nerve 30. The ratio of the magnitude of peak 220 to the magnitude of the highest of depolarization peaks 222 is typically at least 8:1, and is preferably greater than 10:1.

The bottom data line in FIG. 7 shows the combined effect on the activation function due to the summed anode activation function and the activation function due to the cathode. It is noted that the use of the various anodes does not excessively decrease either the magnitude of the desired depolarizing peak 230, or that of the desired hyperpolarizing peak 240 of the combined activation function.

As appropriate, techniques described herein are practiced in conjunction with methods and apparatus described in one or more of the following applications which are assigned to the assignee of the present patent application and incorporated herein by reference:

a US patent application to Gross et al., filed on even date with the present patent application, entitled, "Selective nerve fiber stimulation for treating heart conditions,"

U.S. Provisional Patent Application 60/383,157 to Ayal et al., filed May 23, 2002, entitled, "Inverse recruitment for autonomic nerve systems,"

PCT Patent Application PCT/IL02/00068 to Cohen et al., filed Jan. 23, 2002, entitled, "Treatment of disorders by unidirectional nerve stimulation,"

U.S. patent application Ser. No. 09/944,913 to Cohen and Gross, filed Aug. 31, 2001, entitled, "Treatment of disorders by unidirectional nerve stimulation," and U.S. patent application Ser. No. 09/824,682 to Cohen and Ayal, filed Apr. 4, 2001, entitled "Method and apparatus for selective control of nerve fibers."

It will thus be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. Apparatus for applying current to a nerve having a radius and a longitudinal central axis, comprising:
   a housing, adapted to be placed in a vicinity of the nerve, and shaped so as to define two end walls;
   first and second electrodes, fixed within the housing longitudinally between the end walls; and
   an insulating element, fixed to the housing between the first and second electrodes so as to define a characteristic closest insulating element perpendicular distance to the central axis,
   wherein the first and second electrodes are fixed within the housing so as to define respective first and second closest electrode perpendicular distances to the axis, when the housing is placed in the vicinity of the nerve, and
   wherein the first and second closest electrode perpendicular distances are both greater than the closest insulating element perpendicular distance, and greater than a closest perpendicular distance between the axis and both of the end walls of the housing.

2. Apparatus according to claim 1, wherein the housing is configured such that an arc, defined by an extent that the housing is adapted to surround the nerve, is between about 90 and 270 degrees.

3. Apparatus according to claim 1, wherein the housing is configured such that an arc, defined by an extent that the housing is adapted to surround the nerve, is between about 270 and 359 degrees.

4. Apparatus according to claim 1, wherein the first and second electrodes comprise a cathode and an anode, respectively, fixed to the housing.

5. Apparatus according to claim 4, wherein the apparatus is adapted to be placed on the nerve such that, relative to the anode, the cathode is in a vicinity of the nerve which is proximal to a brain of a subject, the subject including the nerve.

6. Apparatus according to claim 4, wherein the apparatus is adapted to be placed on the nerve such that, relative to the anode, the cathode is in a vicinity of the nerve which is distal to a brain of a subject, the subject including the nerve.

7. Apparatus according to claim 4, wherein the anode is adapted to apply anodal current to the nerve so as to block propagation of action potentials past the anode.

8. Apparatus according to claim 4, and comprising a control unit, coupled to the anode, and adapted to drive the anode to apply current to the nerve at a level configured so as to block propagation past the anode of action potentials in a first set of nerve fibers, and to allow propagation past the anode of action potentials in a second set of nerve fibers, the second set of nerve fibers having characteristic diameters generally smaller than characteristic diameters of the nerve fibers in the first set.

9. Apparatus according to claim 4, wherein a characteristic perpendicular distance of the anode to the axis is within 30% of the characteristic closest insulating element perpendicular distance of the insulating element to the axis of the nerve plus a width of the anode.

10. Apparatus according to claim 1, wherein the insulating element is adapted to be placed in the vicinity of the nerve at a longitudinal site that is between respective longitudinal sites of the first and second electrodes.

11. Apparatus according to claim 1, wherein the insulating element is adapted to be placed in the vicinity of the nerve at a site with respect to the axis of the nerve that is between respective sites of the first and second electrodes, with respect to the axis.

12. Apparatus according to claim 1, wherein the first and second closest electrode perpendicular distances are both at least 30% greater than the closest insulating element perpendicular distance.

13. Apparatus according to claim 12, wherein the insulating element is adapted to be placed in the vicinity of the nerve at a site with respect to the axis of the nerve that is between respective sites of the first and second electrodes, with respect to the axis.

14. Apparatus according to claim 12, wherein the insulating element is disposed in a position with respect to the first and second electrodes so as to guide the flow of current between the first and second electrodes.

15. Apparatus according to claim 1, wherein the housing is configured to form a complete circle around the nerve.

16. Apparatus according to claim 1, wherein the first and second closest electrode perpendicular distances are equal to each other.

* * * * *